(12) United States Patent
Riley et al.

(10) Patent No.: US 6,746,244 B2
(45) Date of Patent: *Jun. 8, 2004

(54) METHOD FOR IMMEDIATELY PLACING A NON-OCCLUSIVE DENTAL IMPLANT PROSTHESIS

(75) Inventors: Robert L. Riley, Vista, CA (US); Philip S. Lyren, Houston, TX (US)

(73) Assignee: Sulzer Dental Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/050,028

(22) Filed: Oct. 22, 2001

(65) Prior Publication Data

US 2002/0090592 A1 Jul. 11, 2002

Related U.S. Application Data

(63) Continuation-in-part of application No. 09/755,240, filed on Jan. 5, 2001, now Pat. No. 6,368,108.

(51) Int. Cl.$^7$ .................................................. A61C 8/00
(52) U.S. Cl. ...................................................... 433/173
(58) Field of Search ................................ 433/172, 173, 433/174, 175, 176, 213, 214

(56) References Cited

U.S. PATENT DOCUMENTS

| 5,123,842 A | * | 6/1992 | Roberts | 433/173 |
| 5,934,906 A | * | 8/1999 | Phimmasone | 433/173 |
| 5,967,783 A | * | 10/1999 | Ura | 433/174 |

* cited by examiner

Primary Examiner—Cary E. O'Connor
(74) Attorney, Agent, or Firm—Christopher R. Kirby, Esq

(57) ABSTRACT

A method for immediately placing a non-occlusive and non-functional temporary dental implant prosthesis in the jawbone of a human patient with the prosthesis having a size and shape of a natural human tooth.

7 Claims, 6 Drawing Sheets

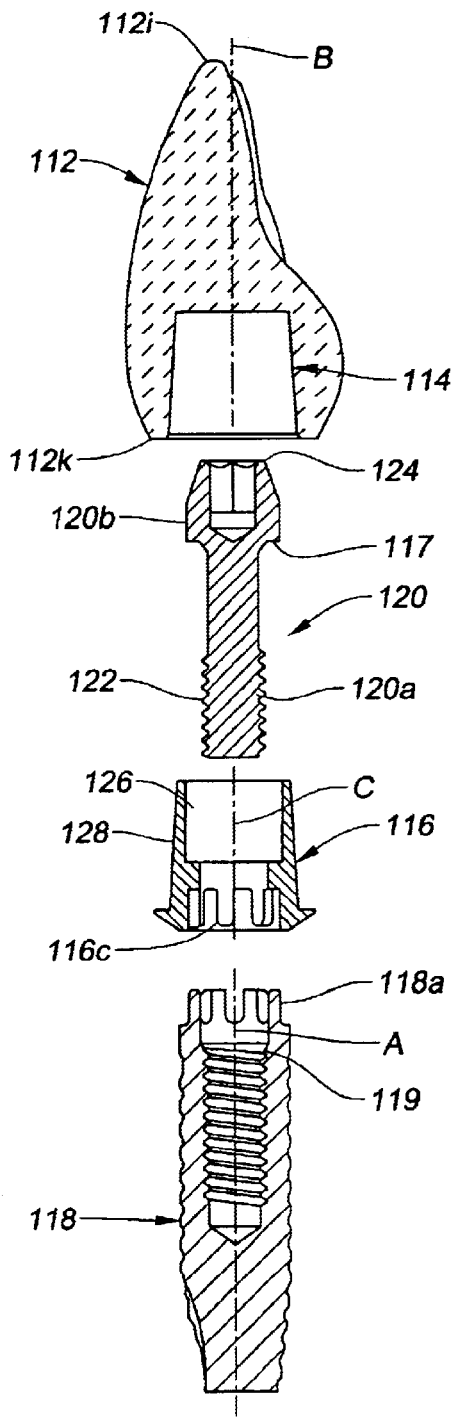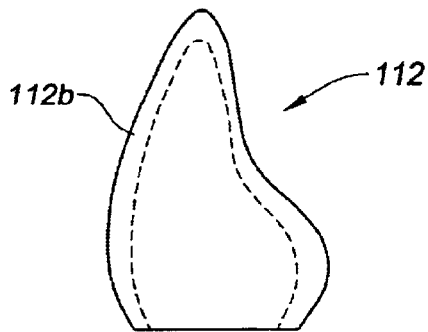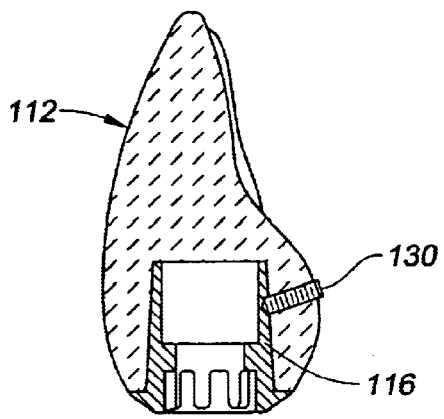
FIG. 5
FIG. 8
FIG. 10

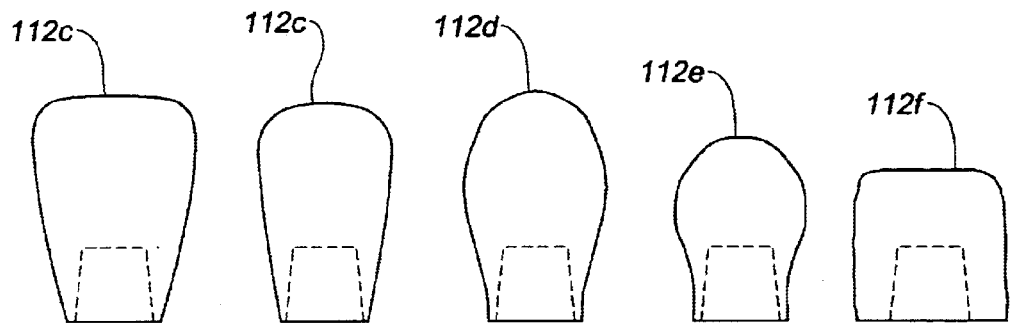
FIG. 9A   FIG. 9B   FIG. 9C   FIG. 9D   FIG. 9E
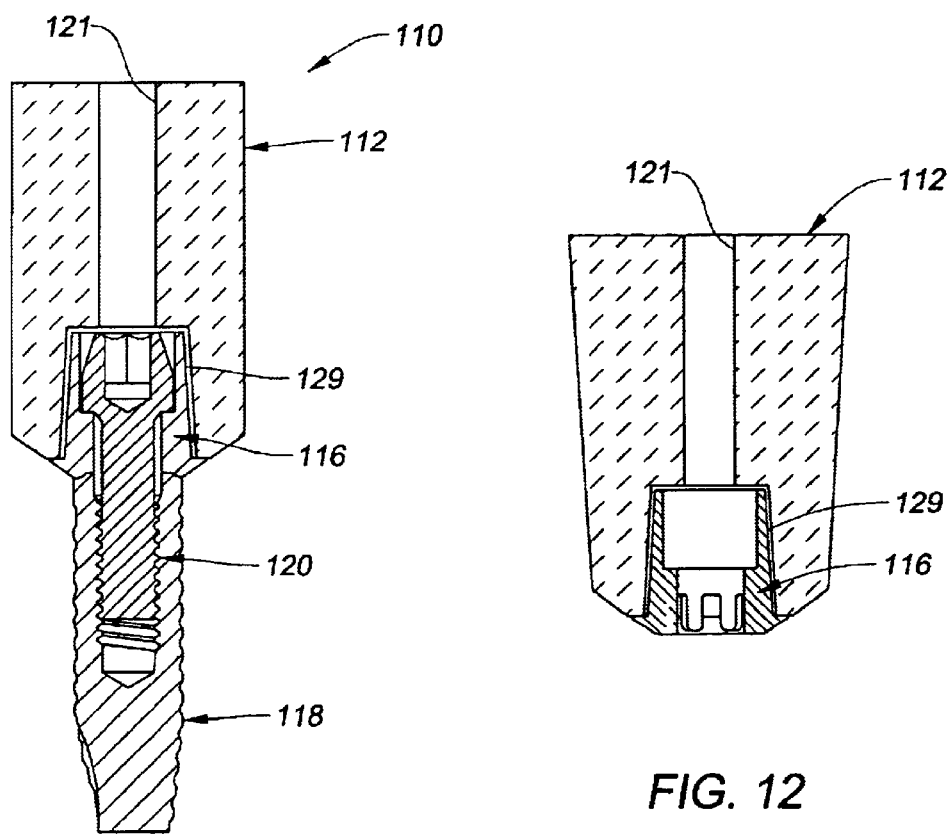
FIG. 11
FIG. 12

METHOD FOR IMMEDIATELY PLACING A NON-OCCLUSIVE DENTAL IMPLANT PROSTHESIS

This is a continuation-in-part of U.S. application Ser. No. 09/755,240, filed on Jan. 5, 2001 now U.S. Pat. No. 6,368,108, invented by Robert L. Riley, et al., and entitled "Method for Immediately Placing a Non-occlusive Dental Implant Prosthesis."

FIELD OF THE INVENTION

The present invention relates generally to a method for immediately placing a non-occlusive and non-functional temporary dental implant prosthesis in the jawbone of a human patient wherein the prosthesis has a size and shape of a natural human tooth.

BACKGROUND OF THE INVENTION

Numerous surgical techniques and methods currently exist to install a dental implant and prosthesis into the jawbone of a human patient. During a conventional surgical procedure, an incision is made along the gingival tissue at the implant site of the patient, a cylindrical bore is drilled into the alveolar bone, and the bore of the bone is tapped. Once the bore is fully prepared, a dental implant is positioned above the implant site and driven into the bore. A healing screw or healing cap is then placed on the coronal end of the implant, and the gingival tissue is sutured. The implant and healing cap remain within the bone for several months as osseointegration and healing occur. After this healing period, a second surgical procedure begins. During this procedure, the gingival tissue is again cut, the implant is re-exposed, and the healing cap is removed. Thereafter, an abutment is affixed onto the top of the implant and a dental prosthesis is affixed to the abutment.

This conventional surgical procedure has many disadvantages. First, during the healing stage while the implant integrates into the bone, a tooth or dental prosthesis will not be present at the implantation site. The patient may have an unsightly gap or otherwise unaesthetic appearance at this location. Further, in some instances, a metallic healing cap or metallic gingival cuff may be left attached to the implant while the tissue and bone heal. The cap and cuff are often visibly exposed in the mouth of the patient and present an unnatural appearance. Further yet in conventional techniques, the patient has to undergo two separate surgical procedures: an initial procedure to implant the implant and a second procedure to remove the healing cap and attach the abutment and prosthesis. Multiple surgical procedures are costly and not desirable for the patient.

Some dental implant systems and surgical techniques attempt to solve the disadvantages associated with conventional implantation procedures. These systems place a prosthetic tooth in occlusion immediately after the implant is driven and positioned in the jawbone of the patient. In this scenario, the patient has a tooth-like prosthesis immediately after the surgery, so aesthetic appearance is no longer a concern. The prosthesis, however, is left in occlusion and thus exposed to immediate loads.

This procedure has disadvantages too. Preferably, movement and disturbance of the implant should be minimal immediately after it is placed in the jawbone. If the prosthesis and attached implant experience loading too soon, then the position of the implant may rotate, loosen, or otherwise move. Such movement could adversely effect the integration and alignment of the implant.

U.S. Pat. No. 5,967,783 (entitled "Threaded Dental Implant with a Core to Thread Ration Facilitating Immediate Loading and Method of Installation") illustrates a dental implant system designed to immediately place and then load a dental prosthesis. As shown in FIG. 1, an implant 10 consists of an elongated unitary body having a main implant portion 12 with external threads 14 and an extended neck portion 16. One disadvantage to this system is that the implant has an elongated implant and neck portions formed from a single piece. A clinician may be required to perform significant modifications to the extended neck portion so it has the correct height or angle to receive the prosthesis. Further, the neck portion could not easily accommodate a screw-retained prosthesis, especially if the neck needed extensive modification. Further yet, the implant is loaded immediately after it is placed; and such loads, as discussed above, may move the implant or otherwise interfere with its orientation or integration. The external threads 14 on the implant further have a specific and specialized thread pattern to help improve resistance of the implant to chewing and compressive forces. This specialized thread pattern may add additional cost to the implant.

The present invention solves the problems discussed with prior methods and dental delivery systems and provides numerous advantages over these prior systems and methods.

SUMMARY OF THE INVENTION

The present invention is directed toward a method for placing a non-occlusive, non-functional temporary dental implant prosthesis immediately after a dental implant is implanted into the jawbone of a human patient. The implant is placed in a conventional manner for edentulous or extraction dental implantation sites. Thereafter, in one embodiment, a separate abutment is connected to the implant; typically such a connection occurs with a screw or cement. A temporary dental implant prosthesis is then attached to the abutment. Most importantly, the temporary prosthesis is placed to be non-occlusive and non-functional; that is to say loads and compressive forces are not transmitted to the implant during normal mastication.

The present method has numerous advantages over prior methods. First, a tooth-shaped temporary prosthesis is connected to implant immediately after the implant is implanted into the jawbone of the patient. As such, the patient does not have an unsightly gap or otherwise unaesthetic appearance at the implantation site. Further, a second, separate surgical procedure is not required since the implant, abutment, and temporary prosthesis are all placed during the first surgical procedure. Further yet, since the prosthesis is left out of occlusion, it is not exposed to immediate loads. Thus, movement and disturbance of the implant is minimized during the integration period. Further yet, the implant and abutment are made from two separate pieces, and the implant is not required to have a special external thread design to help improve resistance of the implant to chewing and compressive forces.

In another embodiment, the prosthesis is formed from an internal metallic core and an external ceramic crown. The crown has a shape that closely resembles the shape of a natural human tooth. The prosthesis can be placed directly on the implant in one step, leaving the patient with a temporary prosthesis that resembles a natural human tooth. This near net tooth shape of the crown will reduce the amount of work, time, and expense required to create a final dental prosthetic restoration. Further, the ceramic used to fabricate this crown is compatible with commercially available porcelains so that the gradients of shade and translucence of the natural tooth can be replicated. Also, the crown may be manufactured to have a size that is slightly smaller than the average natural tooth. This difference in size enables the crown to receive an additional layer of porcelain and then match the exact size of the natural tooth.

As another advantage, the prosthetic teeth of the present invention may be manufactured and sold as a kit. Each kit would include a plurality of prosthetic teeth having different sizes and shapes emulating different sizes and shapes of natural human teeth. A clinician could chose a prosthetic tooth to best match particular needs of a patient.

BRIEF DESCRIPTION OF THE DRAWINGS

The invention will hereafter be described with reference to the accompanying drawings:

FIG. 5 is an exploded cross-sectional side view illustrating an embodiment of a dental prosthetic assembly.

FIG. 8 is a side-view illustrating an embodiment of a near net tooth shaped crown.

FIGS. 9a–9e are views illustrating a plurality of tooth shapes for the near net tooth shaped crown.

FIG. 10 is a cross-sectional side view illustrating an embodiment of a threaded attachment of a near net tooth shaped crown and a core member.

FIG. 11 is a cross-sectional side view illustrating another embodiment of a dental prosthetic assembly.

FIG. 12 is a cross-sectional view of an embodiment of a core with a tapered outside diameter.

DESCRIPTION OF THE PREFERRED EMBODIMENTS

Turning to FIG. 2 and FIGS. 3A–3C, the method of the present invention is discussed in detail. Per block 20 of FIG. 2, the invention may be utilized with both edentulous sites and extraction sites. Further, such sites may be single or multiple restorations. For illustrative purposes, the figures and accompanying description teach application of the present invention to a single tooth extraction implantation site.

As shown in block 22, initially the implantation site is evaluated and prepared. Preferably, the site maintains a gentle elevation of the tooth root to preserve the alveolar housing around the extraction site. A periotome or other small elevators (not shown) may be used to release the periodontal ligament or other soft tissue attachment of the tooth to the surrounding bone. Once the tooth is removed, the socket site should be debrided to remove any soft tissue remnants and then irrigated with sterile saline. A visual inspection of the site can aid in determining the appropriate diameter implant.

Figure 3A:
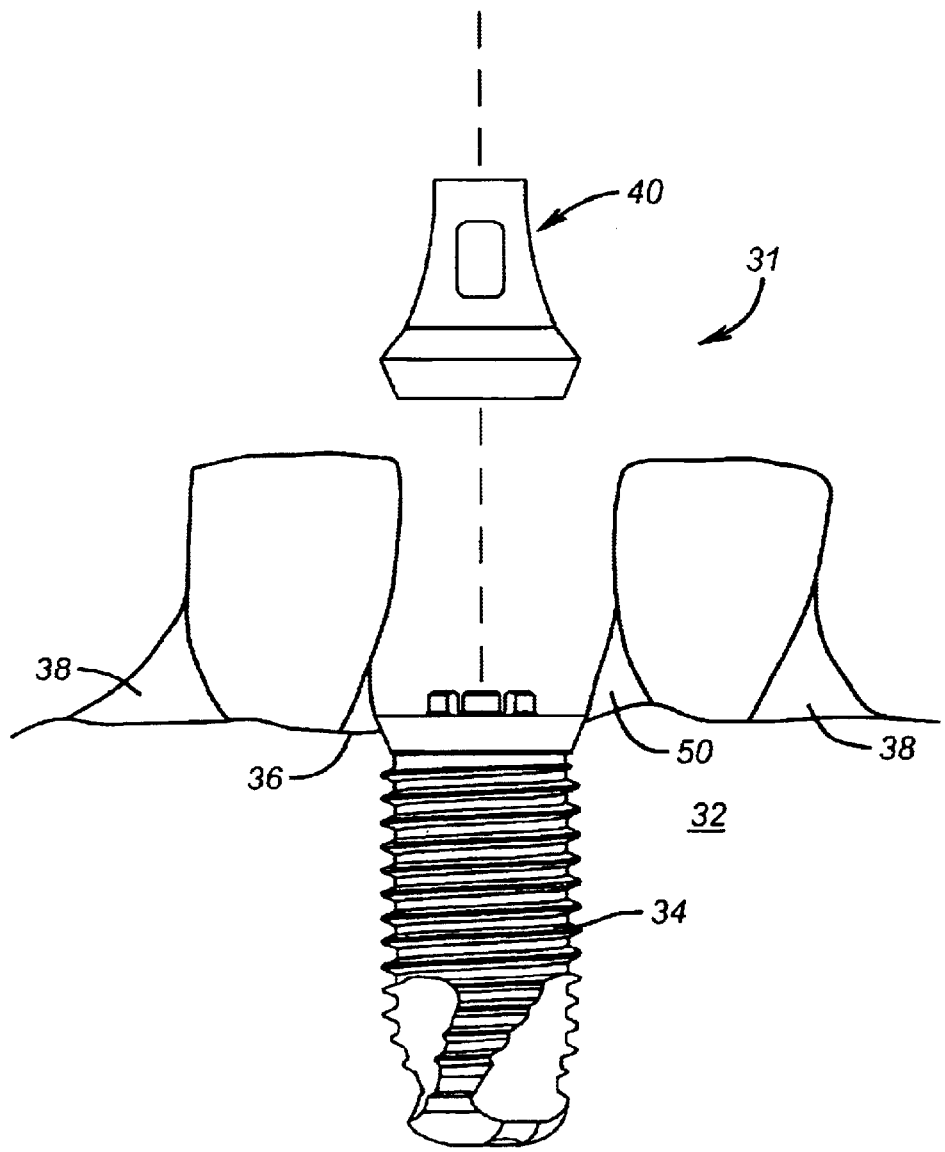
FIGS. 3A–3C show a dental implant, abutment, and temporary prosthesis being implanted according to the method of the present invention.
Figure 3B:
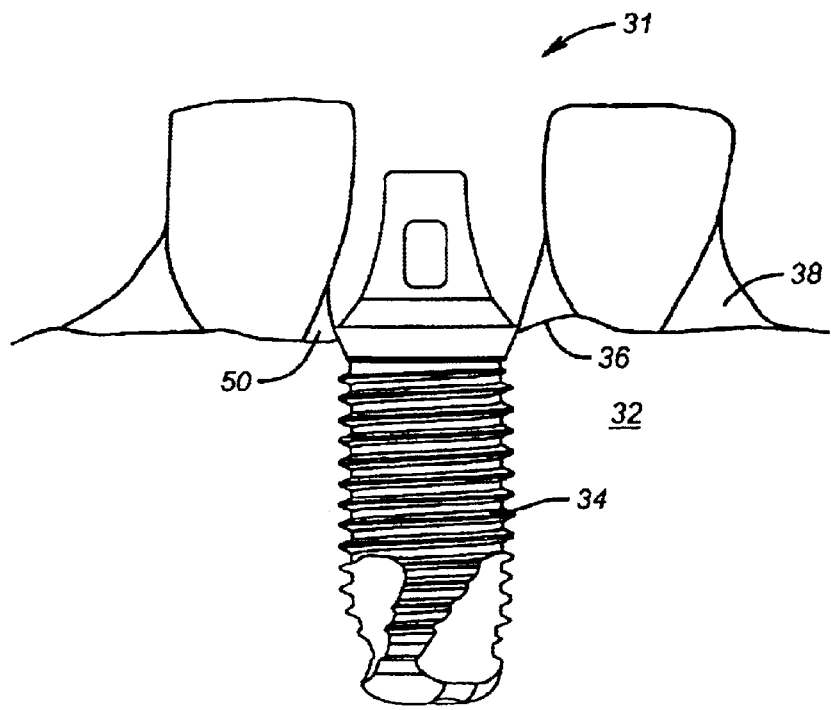
Figure 3C:
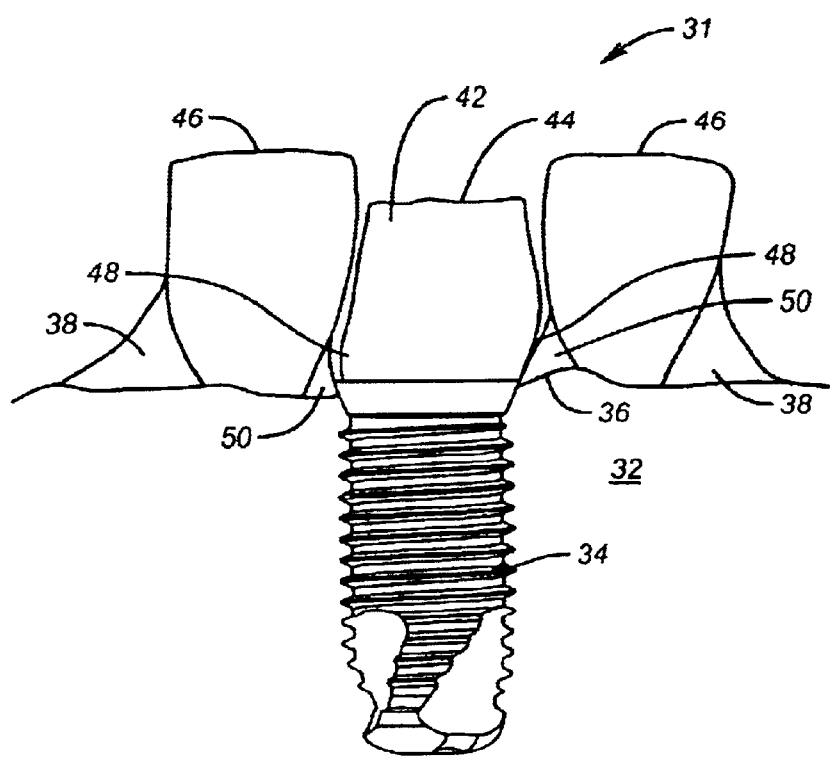

As shown in block 24, the next step is to place the implant into the implantation site 31 (shown in FIGS. 3A–3C). Various implants may be placed using any one of numerous techniques known to those skilled in the art. Preferably, the implant should be dimensioned to sufficiently fill the entire cervical region of the socket. Further, proper orientation and location of the receptor site may be predicated on the initial step of scoring the apex of the socket with a bur or similar instrument. Such scoring provides a recess in the bone 32 to guide a pilot drill (not shown) to a correct, predetermined location.

One example of an implant appropriate for the method of the present invention is a Spline Twist MP-1 implant, manufactured by Sulzer Calcitek Inc. of Carlsbad, Calif. In this instance, the implant 34 can be delivered to the implantation site and inserted via a handpiece and ratchet (not shown). The platform for this implant preferably is placed approximately 1.5 mm below the interproximal bone 36 and below the gingival tissue 38. Placement in this location helps to ensure that the external threads on the implant will be covered by bone and will be at or below the buccal plate.

After the implant is placed, bone grafting may be required. In this instance, a cover screw may be temporarily secured onto the proximal end of the implant to prevent any particulate graft from entering the internal chamber of the implant. Once grafting is completed, the cover screw is removed.

As shown in block 26, the next step is to place an abutment 40 onto the implant. The abutment should be separate from the implant and connectable to the implant using screws, cement, or other techniques known to those skilled in the art. One advantage of having a separate abutment is that various cuff heights and angles may be selected to closely replicate the desired height, angles, and profiles needed. In this manner, the amount of alterations to the abutment is minimized. Of course, the abutment can be modified to meet clinical needs, such as a modification to the overall height or cuff contour.

As shown in block 28, the next step is to place a temporary, non-functional prosthesis 42 on the abutment 40. One important aspect of the present invention is that the prosthesis must be placed in a non-functional or non-occlusive position. Preferably, a top portion 44 of the prosthesis is placed between 0.5 mm and 2 mm below a top 46 of adjacent teeth, as shown in FIG. 3C. In this position, the prosthesis 42 will not be in occlusal loading during the healing period. As such, the prosthesis should be taken completely out of occlusion when the patient is in centric relations and lateral excursions.

After a verification is made that no occlusal loading is present, the prosthesis may be polished and seated with cement or a screw, for example. The patient should be instructed to avoid chewing in the implantation area of the prosthesis while the implant is allowed to heal. Typically, the healing period will occur from about one month to about nine months.

As one important advantage of the method of the present invention, gingival tissue should be contoured around the temporary prosthesis to maintain a natural shape and appearance. Gingival tissue, for instance, can be sutured around a cervical portion 48 of the prosthesis (as shown in FIG. 3C) if the implantation site is edentulous and an incision was made to expose the bone. Suturing the tissue in this manner helps to maintain and develop soft tissue contours around the prosthesis. Suturing, though, may not be necessary if the implantation site is from an extraction and the abutment and temporary prosthesis completely fill the hole left from the natural tooth.

As yet another important advantage of this method, hard and soft tissue contours adjacent to the implant and prosthesis should be maintained to retain interdental papilla 50.

As shown in block 30, after the healing period has elapsed, the temporary prosthesis is removed from the abutment and a permanent prosthesis is connected. The permanent prosthesis is functional and in occlusion in the jawbone of the patient. An experimental trial was conducted on a small group of patients to determine the feasibility of a method in accordance with the present invention. The method was used on 55 patients: 19 males and 36 females. The ages of the males ranged from 2655 years and females from 17–78 years. All implants were placed from the premolar forward. In the male group, one implant was lost due to trauma. In the female group, one implant was mobile after six weeks and required removal. The male patient was removed from the combine group resulting in a total of 54 patients. Survival rate was approximately 98.15%.

Based on analysis of the patients in this trial, the method of the present invention appears to be a very efficacious for replacing missing anterior teeth. Further evaluation is being conducted in a larger population of patients but shows dramatic promise for the effective replacement of lost anterior teeth. This technique has not been employed to posterior teeth beyond the second premolar. It may be effective in these regions as well; however, the increased occlusal force and protection factors must be considered. The following two cases are examples from the experimental trial.

CASE I

A 74-year old female had a fractured, non-salvageable first premolar. The tooth was gently elevated, keeping the soft tissue and hard tissue contours intact. There was no elevation of the soft tissue. The socket site was checked to make sure the buccal plate was intact. Direct visualization and palpation were used to identify the inter-septal buccal plate rim. In this case, the site was prepared via harvest instrumentation. The platform of the implant was set approximately 1–1.5 mm below the level on the inter-septal bone; such placement ensured the shoulder of a 2 mm abutment to be approximately 1 mm below the level of gingival cuff rim. This placement also ensured that the soft tissue would be supported to maintain its position and would allow for maximum emergence of the temporary prosthesis (or provisional). The temporary prosthesis was seated with temporary cement and taken out of occlusion. It was then allowed to heal for 16 weeks. After the healing period, this patient was then sent to another doctor for fabrication of the final restoration. The position of the papilla was maintained as well as that of the buccal gingival contour, allowing for maximum tissue esthetics and excellent emergence profile.

CASE II

A 47-year old man had tooth #9 that was super-erupted and mobile. Due to his present occupation, aesthetics and a quick remedy were necessary. The tooth was atraumatically removed and the socket site debrided. The position and loss of the gingiva in relation to the adjacent teeth was important here. The implantation site was prepared in a sequential fashion, utilizing drills and hand instrumentation. The implant was then seated in place, positioning the platform approximately 1–1.5 mm below the level of crestal bone. Here, the width of the socket determined the diameter of the implant, and care was taken not to perforate the buccal plate. The abutment was seated to place, the shoulder being approximately 1 mm below the crest of the gingival collar. The temporary prosthesis was placed and positioned to be out of centric occlusion and excursive movement. The tissue and implant was allowed to heal. After the normal healing time had transpired, the implant was restored.

The experimental trial demonstrates numerous advantages to the method of the present invention. First, the patient does not need to wear a removable prosthesis during the healing period. Second, the patient leaves the implantation procedure with a fixed provisional prosthesis or tooth. This fact alleviates any apprehension that the patient may have about the loss of anterior teeth and provides an esthetically pleasing option. Third, preservation of the implantation site's soft and hard tissue contours are maintained, improving the esthetics of the temporary and permanent prostheses. This preservation also allows for the final restoration of soft tissue such that no sutures are required at the surgical site. Further, the patient receives a temporary prosthetic tooth the same day as surgery, and no unsightly gaps or unnatural appearances occur in the mouth of the patient at the implantation site.

Figure 1:
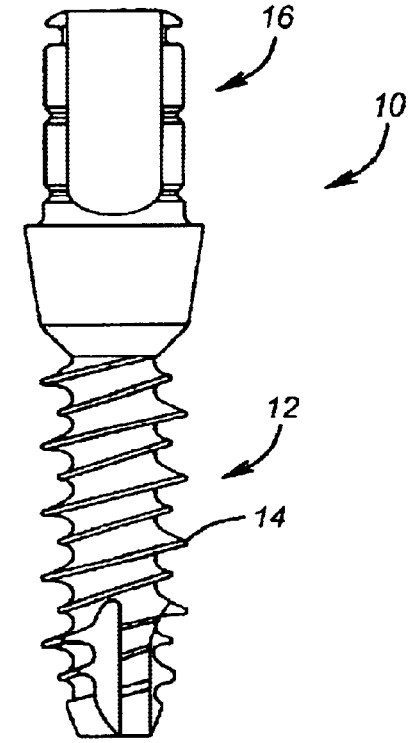
FIG. 1 is a side-view, partially in cross section, of a prior art dental implant system.
Figure 2:
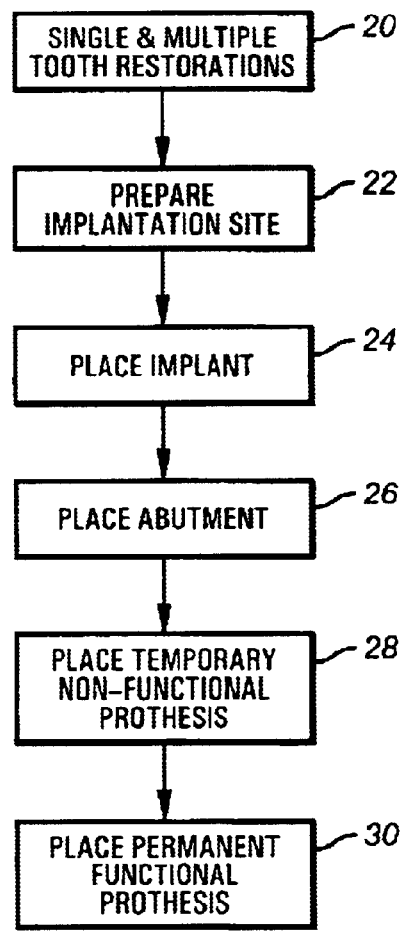
FIG. 2 is a block diagram illustrating the method of the present invention.

Blocks 24 and 26 in FIG. 2 discuss an abutment and prosthesis placed on the implant in two separate steps. In an alternate embodiment of the present invention, these steps may be combined. The abutment and prosthesis may be pre-connected and placed on the implant in one step. Further, regardless whether the abutment and prosthesis are pre-connected or separate, the prosthesis may be manufactured to have a tooth shape. These alternate embodiments are discussed below.

Figure 4:
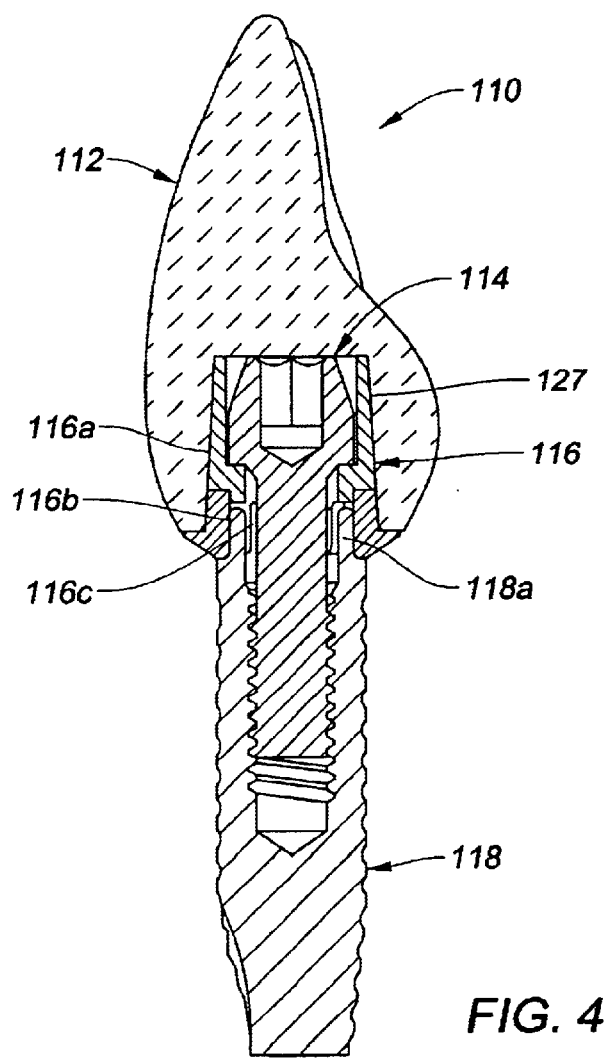
FIG. 4 is a cross-sectional side view illustrating an embodiment of a dental prosthetic assembly according to one embodiment of the invention.

FIGS. 4 and 5 show a tooth-like prosthesis 110 having a near net tooth shaped crown 112 and a metallic core 116. The crown 112 has an internal bore 114 to receive the core and is manufactured to have a size and shape of a natural human tooth.

As shown, a threaded fastener or screw 120 connects the core 116 to the anchor 118. The fastener includes a first end 120a having threads 122 and a second end 120b having a polygonal socket 124. A tool (not shown) can be inserted into socket 124 to turn fastener 120 into threaded engagement with a threaded bore 119 in anchor 118. Core 116 includes a screw bore 126 and a screw seat 128.

Screw bore 126 includes an axis C that extends substantially co-axially with an axis A of anchor 118. Fastener 120 is inserted through core 116 and threaded into anchor 118. When fully seated, a shoulder 117 of second end 120b of threaded fastener 120 is seated on screw seat 128 within core 116. Further, an axis B passes through the near net crown 112 from an incisal edge 112i to a cervix 112k.

In FIG. 5, all axes (A, B, and C) are longitudinal and co-axial. In another embodiment of the invention, the crown, however, may be angled to provide proper alignment or angular correction of the prosthesis in the jawbone of the patient. Axis B, for example, could be canted or angled to provide angular offset for the crown.

The core 116 is preferably formed of a material selected for fatigue strength suitability such as a metal, like titanium or titanium alloy. The metal core can be fabricated with various shapes, such as a cylindrical geometry (shown in FIG. 6) or a frusto-conical geometry (shown in FIG. 7). Further, the core may be formed from one piece (as shown in FIG. 4, for example) or formed from two or more pieces. FIG. 4 shows a core formed from two pieces: a core body 116a and a core cuff 116b.

Preferably, the core anti-rotationally engages the implant. The anti-rotational engagement between the core and implant may occur with numerous techniques known to those skilled in the art. Some examples of these techniques include male and female polygonal projections or locking tapers. FIGS. 4 and 5 show a spline connection between the core and implant. In this connection, a plurality of splines 116c on the core engage a plurality of mating splines 118a on anchor 118.

Figure 6:
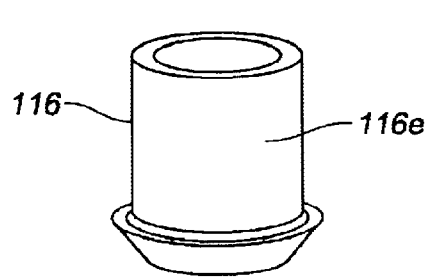
FIG. 6 is a perspective view illustrating an embodiment of a core member.
Figure 7:
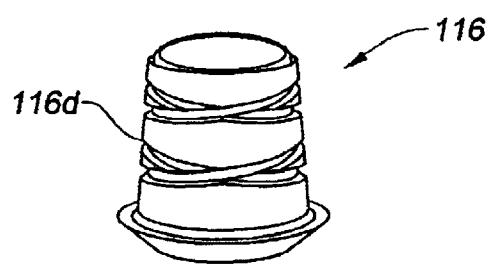
FIG. 7 is a perspective view illustrating another embodiment of a core member.

The outer surface of the core may have various textures, coatings, and configurations. FIG. 6, for example, shows core 116 with a textured coating 116e on the outer surface. FIG. 7 shows core 116 having a plurality of grooves 116d. The various textures and coatings can enhance the strength of connection between the core and crown.

While ceramics can be strong, they are often brittle. The addition of a metallic core adds strength to the overall assembly. This added strength is especially important at the implant interface where forces are transferred from the restoration to the anchoring implant.

Crown 112, FIG. 8, is formed of an aesthetic suitable material, such as a ceramic material, an unfired ceramic material, a polymer material, or a combination of ceramic and polymer materials. Preferably, the crown is made from a ceramic, such as aluminum oxide, zirconium oxide, or a composite thereof. These materials can be made to have mechanical strength sufficient to support occlusal forces and are relatively inert when exposed to body fluid and tissues. These materials also allow for the addition of porcelain to their surface to provide shading to the unique color of the adjacent natural dentition. A clinician, laboratory, or the like may add a layer of porcelain to the outer surface of the crown to match the aesthetics of adjacent natural teeth. The crown can also be manufactured and sold with a thin layer of porcelain 112b already applied to its surface. This latter application facilitates minor modifications to the final prosthetic restoration.

In one embodiment, the crown may be manufactured to have a size that is slightly smaller than the average natural tooth. For example, the crown can be manufactured to have an outside surface or outside diameter that is 0.5 mm to 1.5 mm smaller than the natural tooth to be replaced. This difference in size enables the crown to receive an additional layer of porcelain and then match the exact size of the natural tooth.

One important advantage of the present invention is that the crown is manufactured to have shapes approximately equal to the natural shapes of human dentition. The crowns, manufactured in these shapes are thus prefabricated and sold to clinicians, laboratories, and the like in the shape of human teeth. Since ceramic materials are typically difficult to shape using machining techniques, the present invention significantly reduces or completely eliminates the amount of machining required to create the shape and size of the final prosthetic restoration.

Crown 112 may be provided in a kit to have a plurality of different sizes and shapes that mimic the sizes and shapes of natural human teeth. These shapes, for example, could include tooth shapes such as an incisor 112c, FIGS. 9a, 9b, a canine 112d, FIG. 9c, a premolar 112e, FIG. 9d and a molar 112f, FIG. 9e.

Crown 112 may be attached to core 16 by various means known to those skilled in the art. In FIG 4, the bore 114 in the ceramic crown 112 is made slightly larger than the outside diameter of the core 116. This difference in size creates a cement gap 127. The cement gap is a space for dental cement that holds the crown to the core. In FIG. 10, an alternative connection method is shown, a threaded fastener 130, such as a set screw, is used to attach crown 112 to core 116.

FIGS. 11 and 12 show another embodiment of the present invention and in particular illustrate an alternative way to attach crown 112 to core 116. A layer of material 129 is provided between the crown and the core. This material is suitable for bonding the two components when the components are heated. This layer of material may be a heat activated adhesive or may be formed from precious metals, such as gold, silver, platinum, palladium, or alloys formed from these metals.

In the preferred embodiment, the core is fabricated from gold (or a gold alloy) and then gold (or a gold alloy) is used to bond the core and the crown. Gold is advantageous since it is both strong and biocompatible. Further, dental gold alloys are capable of withstanding higher temperatures than titanium.

Preferably, the gold is applied to the inner bore in the crown. The gold core and crown are then connected together, and heat is applied to bond them permanently together. The bonding may occur after an outer layer of porcelain is applied to the crown and subsequently heated or baked to bond the porcelain to the ceramic crown. This latter step often occurs since dental laboratories bake shades of porcelain onto the ceramic crown to match color of natural teeth. The heat during this operation melts or activates the layer of material 129. After the prosthesis is heated, the porcelain baked, and the crown and core bonded, the prosthesis is ready to be implanted into the jawbone of the patient. As shown in FIGS. 11 and 12, a hole 121 may be left in the crown to provide access to the screw 120.

Gold soldering or a brazing process can be used to join the core to the crown. A dental laboratory, for example, can add the soldering or brazing gold, or the gold can be supplied as a preform coating installed during the manufacturing stage. The preform coating can also be added using an electroplating process that metallizes the surface of the internal bore and bonds the crown and core.

What is claimed is:

1. A method for placing a temporary dental prosthesis in the jawbone of a human patient, the method comprising the steps of:
   implanting a dental implant into the jawbone of the patient;
   providing a temporary prosthesis having an internal metallic core and an external ceramic crown, wherein the temporary prosthesis is prefabricated to have an anatomical size and shape of a natural human tooth;
   connecting the temporary prosthesis to the implant such that the temporary prosthesis is in a non-occlusive and non-functional position;
   leaving the temporary prosthesis connected to the implant for a healing period between one and nine months;
   removing the temporary prosthesis after the healing period; and
   replacing the temporary prosthesis with a permanent prosthetic tooth that is in an occlusive and functional position in the jawbone.

2. The method according to claim 1 further comprising the step of providing the temporary prosthesis to have a prefabricated shape selected from one of incisor, canine, premolar, or molar.

3. The method according to claim 2 wherein the temporary prosthesis has a color of human teeth.

4. A method for placing a dental prosthesis in the jawbone of a human patient, the method comprising the steps of:
   implanting a dental implant into the jawbone of the patient;
   providing a temporary prosthetic tooth having an internal metallic core and an external ceramic crown, wherein the temporary prosthetic tooth is prefabricated to have an anatomical size and shape of a natural human tooth;
   connecting the temporary prosthetic tooth to the implant;
   positioning the temporary prosthetic tooth in a non-occlusive and nonfunctional position in the jawbone;

leaving the temporary prosthetic tooth connected to the implant for a period between one and nine months; and removing the temporary prosthetic tooth and replacing it with a permanent prosthetic tooth that is in an occlusive and functional position in the jawbone.

5. The method according to claim 4 in which a top of the temporary prosthetic tooth is positioned between 0.5 mm and 2 mm below a top of adjacent teeth.

6. The method according to claim 5 in which no loading occurs on the temporary prosthetic tooth when the patient is in centric relations and lateral excursions.

7. The method according to claim 4 in which no loading occurs on the temporary prosthetic tooth during mastication by the patient.

* * * * *